United States Patent
Davis et al.

(10) Patent No.: US 7,020,525 B1
(45) Date of Patent: Mar. 28, 2006

(54) FLEXIBLE ELECTRICAL INTERCONNECT FOR AN IMPLANTABLE MEDICAL DEVICE

(75) Inventors: Dion F. Davis, Palmdale, CA (US); Charles Markham, Newhall, CA (US)

(73) Assignee: Pacesetter, Inc., Sylmar, CA (US)

( * ) Notice: Subject to any disclaimer, the term of this patent is extended or adjusted under 35 U.S.C. 154(b) by 711 days.

(21) Appl. No.: 10/172,249

(22) Filed: Jun. 14, 2002

(51) Int. Cl.
*A61N 1/18* (2006.01)

(52) U.S. Cl. .................... 607/36; 607/5; 607/9
(58) Field of Classification Search .......... 607/36, 607/9, 2, 4, 5; 381/322; 128/899
See application file for complete search history.

(56) References Cited

U.S. PATENT DOCUMENTS

| | | | | |
|---|---|---|---|---|
| 4,006,748 A | * | 2/1977 | Schulman | 607/36 |
| 4,539,440 A | | 9/1985 | Sciarra | 179/107 |
| 4,991,578 A | * | 2/1991 | Cohen | 607/2 |
| 5,439,482 A | * | 8/1995 | Adams et al. | 607/5 |
| 5,456,698 A | * | 10/1995 | Byland et al. | 607/36 |
| 5,466,254 A | | 11/1995 | Helland | 607/123 |
| 5,645,586 A | * | 7/1997 | Meltzer | 623/11.11 |
| 5,662,691 A | * | 9/1997 | Behan et al. | 607/32 |
| 5,683,434 A | | 11/1997 | Archer | 607/36 |
| 5,825,896 A | | 10/1998 | Leedom | 381/69 |
| 6,012,580 A | * | 1/2000 | Peters et al. | 206/470 |
| 6,558,621 B1 | * | 5/2003 | Banks et al. | 422/28 |

* cited by examiner

*Primary Examiner*—Robert E. Pezzuto
*Assistant Examiner*—Deborah Malamud

(57) ABSTRACT

A flat ribbon cable for interconnecting electrical components mounted in mating clamshell enclosure halves of an implantable cardiac stimulation device. The ribbon cable is configured to butterfly open when the enclosure is opened and interconnect components in each half without undergoing undue mechanical stress as the halves are distanced. The ribbon cable is also configured to fold together when the enclosure halves are mated together, without bending, in a very compact manner so as to occupy minimal room in the enclosure when the device is ready for implantation thus preserving more room for batteries, capacitors, and other electrical devices providing the sensing and stimulation functions of the device and/or allowing the overall space envelope of the stimulation device to be reduced.

29 Claims, 4 Drawing Sheets

FIG. 3
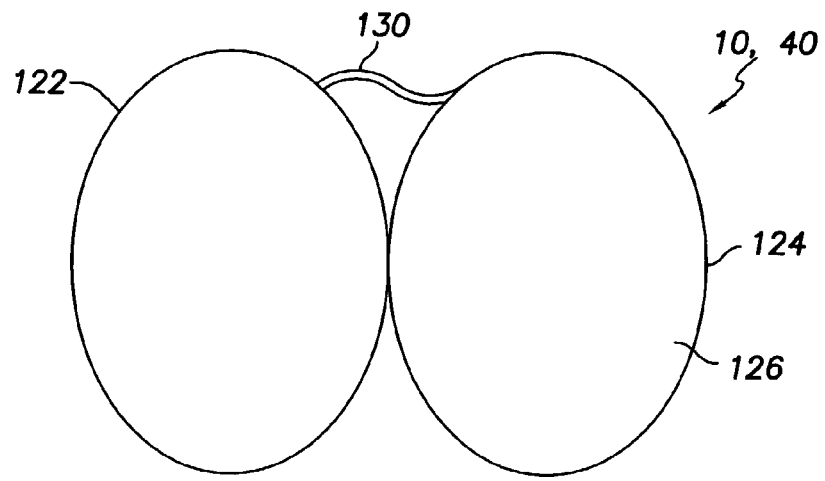
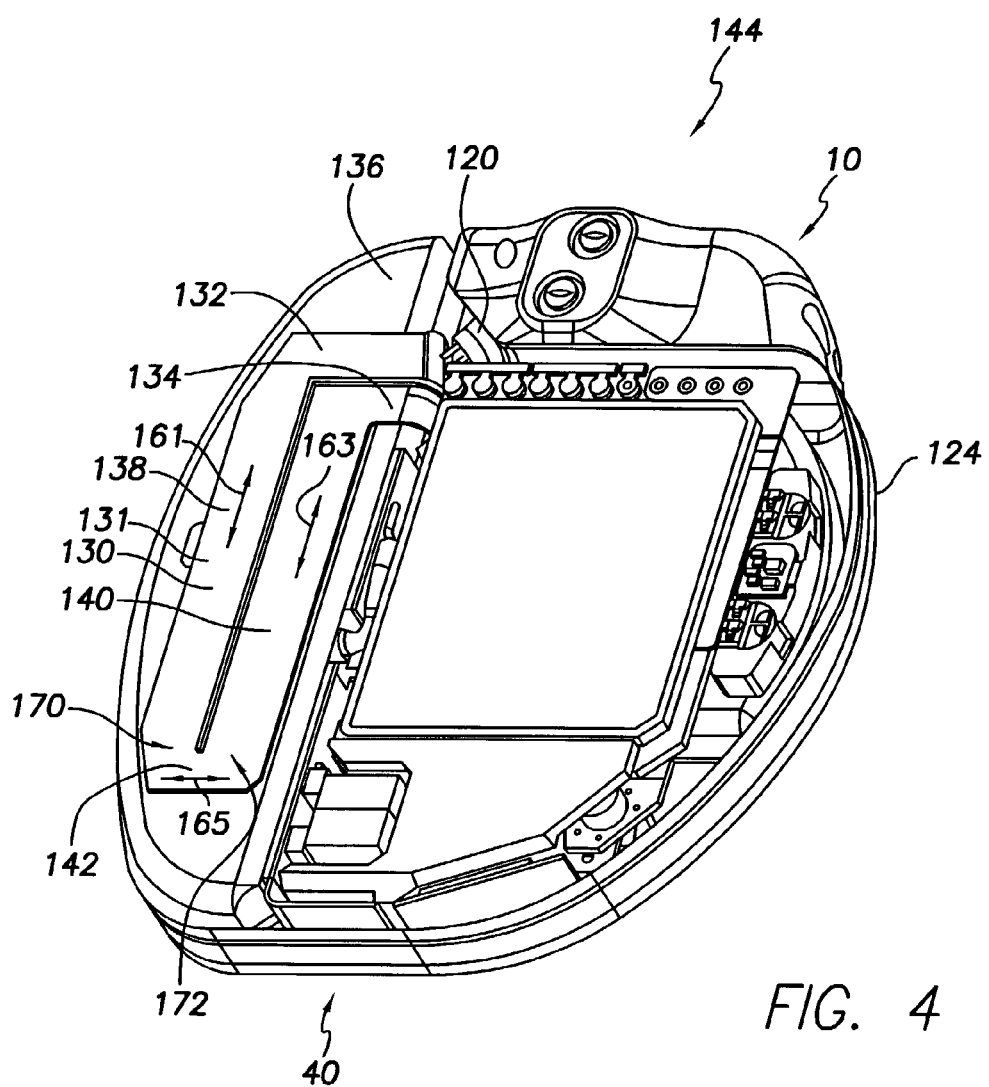
FIG. 4

FLEXIBLE ELECTRICAL INTERCONNECT FOR AN IMPLANTABLE MEDICAL DEVICE

FIELD OF THE INVENTION

The present invention relates to the field of implantable medical devices, such as pacemakers and intra-cardioverter defibrillators (ICD's) and, in particular, to a flexible electrical interconnect of such a configuration as to reliably interconnect two components in a low profile manner.

BACKGROUND OF THE INVENTION

Implantable medical devices are being used increasingly to monitor and assist functioning of the patient's organs. These types of devices includes cardiac stimulation devices e.g., pacemakers and ICDs, as well as insulin pumps and other mechanical devices. These devices are increasingly complicated thereby requiring increasingly complicated circuitry to be implanted in a casing within the body. Implanted devices are more convenient for the patient as an implanted device reduces the need for the patient to wear and accommodate an external device in their daily life.

Implantable devices, such as implantable cardiac stimulation devices, typically include a variety of electronic components such as batteries, sensing and stimulation circuits, microprocessors/controllers, and capacitors contained within a biocompatible enclosure. The enclosure is often made up of two clamshell halves which can be hingedly attached. The electrical components must generally be secured to a substrate such that the electrical components are secured to accommodate the movement of the implantable device when implanted within the patient. Consequently, when the casing is comprised of two clam shell halves, the electrical components are often secured to the interior surfaces of both of the clam shell halves. Both halves typically hold electrical components and the clamshell enclosures are typically positioned in an open configuration during manufacture or service of the device. Once the device is completed and ready for implantation, the clamshell halves are typically closed so as to be adjacent each other and essentially parallel. The clamshell halves form a hermetic seal in the closed position to exclude body fluids from the device electronics.

Many implantable medical devices, such as cardiac stimulation devices, are preferably as small as possible in order to minimize impact on the patient. The larger the casing, the more uncomfortable the implanted device is for the patient. The control, sensing, and stimulation circuitry, as well as the power supply, take up a considerable amount of room in the device enclosure. It is for these reasons that electrical components are typically installed in both halves of a clamshell enclosure. The electrical components in each clamshell half must typically be interconnected with electrical components in the opposing half. This imposes a requirement for an electrical interconnection that interconnects the various components in both halves with the enclosure in both the open and closed configuration.

Several methods are known in the art for interconnecting components in a plurality of relative positions. Slidable contacts, such as slip rings, are known to provide electrical contact throughout a range of sliding or rotational movement. However, slidable contacts are prone to corrosion at contact surfaces which can increase impedance and reduce signal transmission. In addition, slidable contacts, capable of conducting the relatively high voltage shocks that many implantable cardiac stimulation devices provide, tend to be large and occupy an undesirably large amount of the interior volume of the device.

Flat, straight ribbon cable is another known device for maintaining electrical contact between two electrical assemblies in relative motion. However, ribbon cable of known configurations is problematic with implantable medical devices as described above. In particular, the adjacent placement of the two clamshell halves in the closed position forces the ribbon cable into a tight bend such that the ribbon cable folds on itself. This places mechanical stress on the conductors and insulating material of the ribbon cable. This stress can compromise the electrical insulating ability of the insulation and lead to shorting and cross-talk between individual conductors of the cable. Further, sharp bends and other mechanical stresses can also result in the conductors breaking. In addition, the ribbon cable can only bend on itself to a limited radius and this bend or fold occupies an undesirably large interior volume in the device.

With most implantable medical devices and, in particular, implantable cardiac stimulation devices, the potential risks of conductors that are corroded or damaged as a result of the manner in which electrical components in each of the halves are interconnected is quite high. Electrical components may become disconnected potentially rendering the device inoperable. Consequently, many devices have made greater space allowances for electrical interconnect conductors which thereby either increases the size of the implantable medical device or decreases the available space for other necessary electrical components.

From the foregoing it will be appreciated that there is a continuing need in the implantable medical device field for an interconnection mechanism that reliably interconnects electrical components contained in opposing enclosure halves both in an open configuration and in a closed configuration as well as while moving between the two in a low profile fashion. The interconnection mechanism should not be under undue mechanical stress in either the open or closed configurations. There is a further need for an electrical interconnect that is durable and is not subject to the contact corrosion problems of slip-ring type contacts.

SUMMARY OF THE INVENTION

The aforementioned needs are satisfied by the casing of the present invention which, in one aspect, comprises a first and second enclosure halves each defining an interior space that retains a first and a second plurality of electrical components respectively. The casing further includes an electrical interconnect cable assembly that has a plurality of conductors surrounded by insulation. The plurality of conductors are preferably insulated from each other by the electrical interconnect cable and the plurality of conductors electrically interconnect the first plurality of electrical components with the second plurality of electrical components.

The electrical interconnect cable is preferably configured such that when the first and second enclosure halves are positioned together, the plurality of conductors each have a first and a second leg that extend in directions that are substantially parallel to each other in at least one plane. Moreover, the electrical interconnect cable is also preferably configured such that the first and second legs of each of the conductors are interconnected by a transverse section that extends in a direction transverse to the parallel directions of the first and second legs in the at least one plane.

Consequently, the electrical interconnect cable is preferably assembled such that the first and second legs can be positioned side-by-side in at least one plane so as to reduce the overall thickness of the electrical interconnect assembly. Moreover, due to the addition of the transverse section interconnecting the legs, allows for a change of direction of up to 180 degrees between the first and second legs to be accomplished in two smaller changes of direction thereby reducing the stress on the plurality of conductors within the electrical interconnect cable.

The first and second legs of the electrical interconnect cable are preferably flexible such that when the first and second enclosure halves are positioned in an open, side-by-side configuration, the first and second legs extend laterally outward from the transverse section. The first and second legs thereby extend laterally between the first and second enclosure halves when the first and second enclosure halves are in the open configuration thereby keeping the first and second plurality of electrical components interconnected.

Hence, the casing of the present invention allows for the interconnection between electrical components mounted in a two enclosure halves in a manner that does not require sharp bends in the conductors and also does not require the conductors to be stacked on top of each other. Hence, the electrical interconnection is thus both more reliable and consumes less space within the closed enclosure while still permitting the electrical components to remain interconnected when the enclosure halves are separated. These and other objects and advantages will be more apparent from the following description taken in conjunction with the accompanying drawings.

BRIEF DESCRIPTION OF THE DRAWINGS

Further features and advantages of the present invention may be more readily understood by reference to the following description taken in conjunction with the accompanying drawings, in which:

FIG. 3 is a top view of a cardiac device provided with a flexible electrical interconnect in an open position;

FIG. 4 is a perspective cutaway view of a cardiac device provided with one embodiment of a flexible electrical interconnect in the closed or implantation ready state.

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
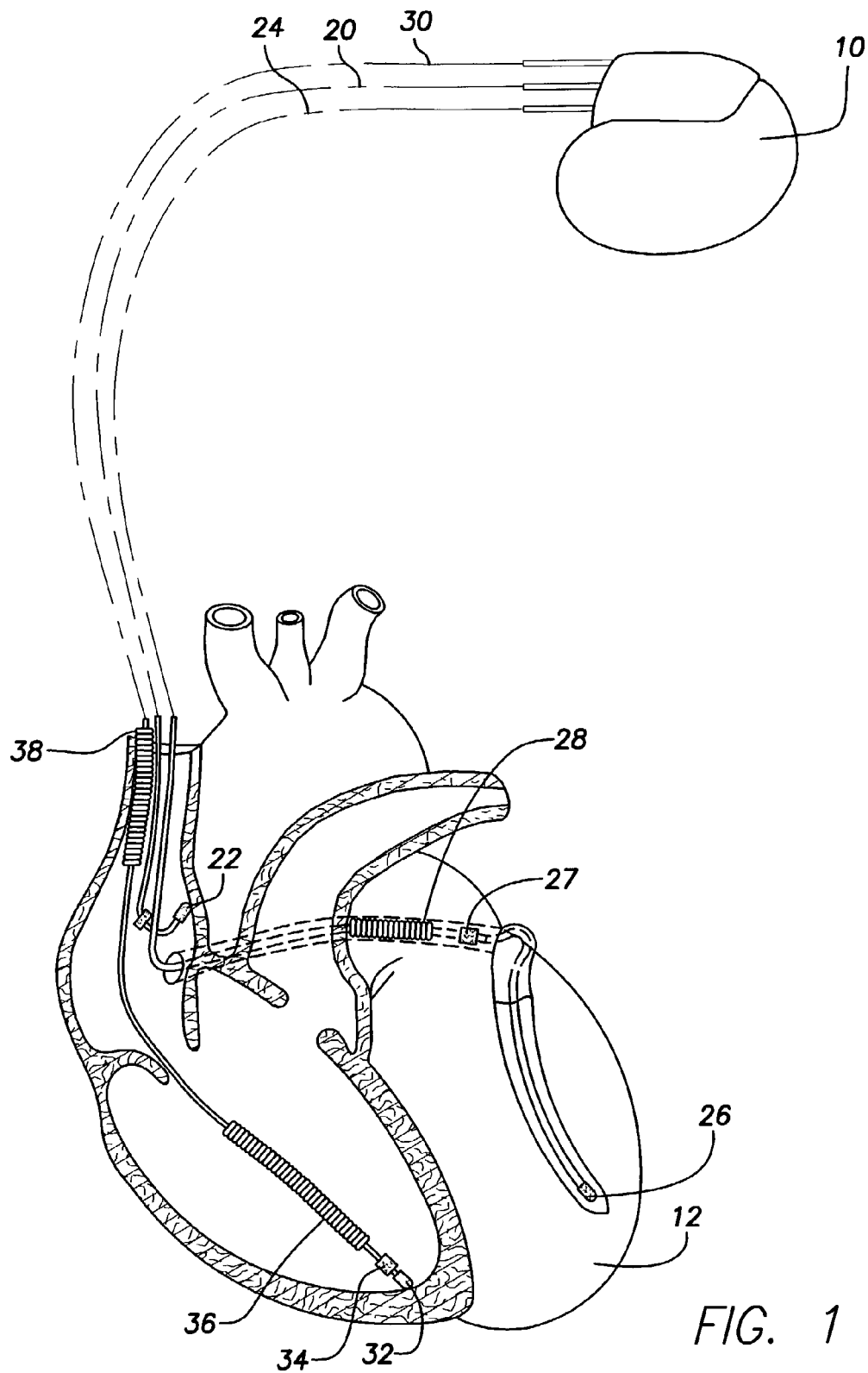
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. Pat. No. 5,466,254, "Coronary Sinus Lead with Atrial Sensing Capability" (Helland), which patent is hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 2:
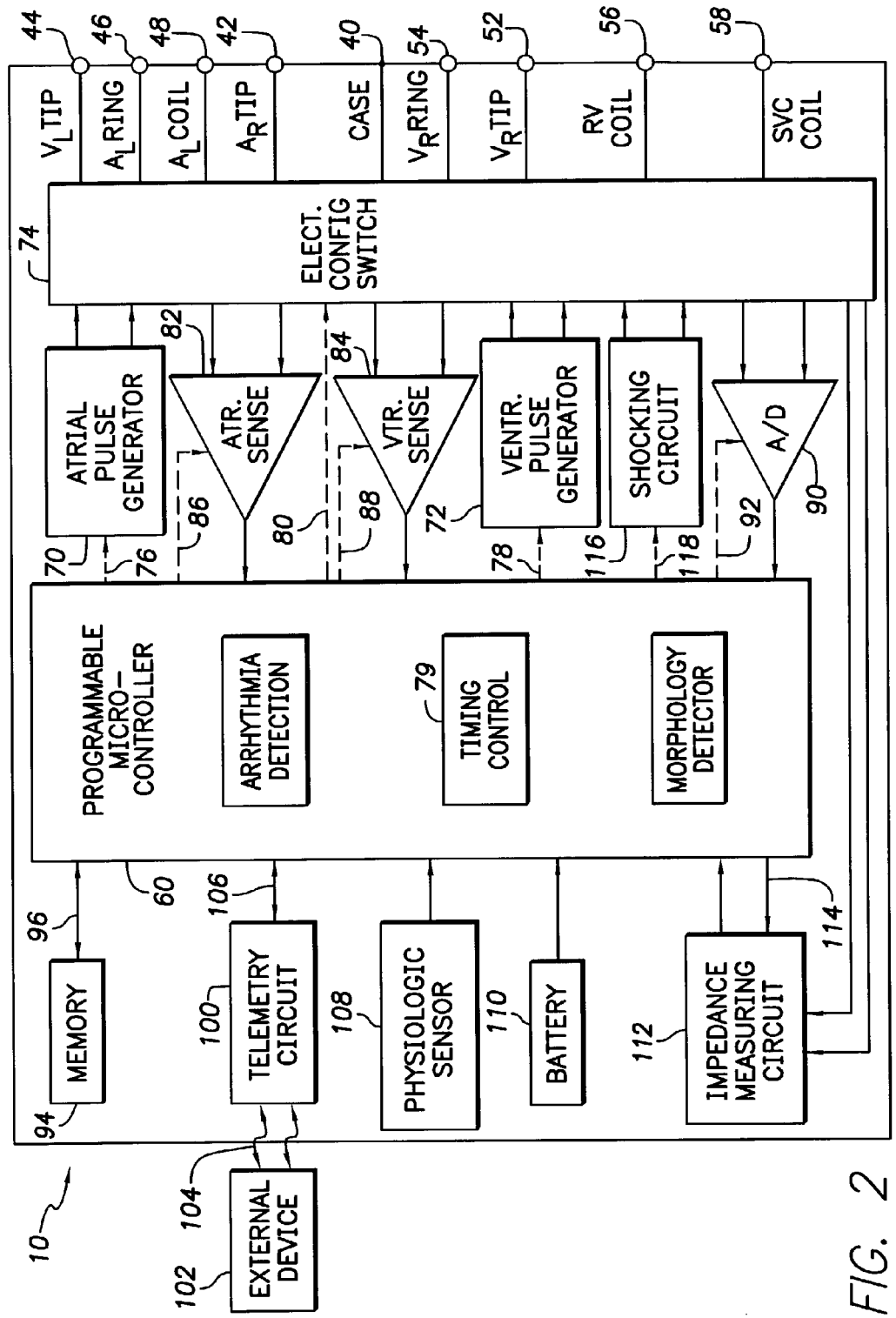
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector 120 (FIGS. 4 and 5) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector 120 includes at least a right atrial tip terminal ($A_R$ TIP) 42 adapted for connection to the atrial tip electrode 22.

To achieve left chamber sensing, pacing and shocking, the connector 120 includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector 120 further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart 12, the atrial and ventricular pulse generators 70 and 72 may include dedicated, independent pulse generators, multiplexed pulse generators, or shared pulse generators. The pulse generators 70 and 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart 12. Accordingly, the atrial (ATR. SENSE) and ventricular (VTR. SENSE) sensing circuits 82 and 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit 82 and 84 preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits 82 and 84 are connected to the microcontroller 60 which, in turn, are able to trigger or inhibit the atrial and ventricular pulse generators 70 and 72, respectively, in a demand fashion in response to the absence or presence of cardiac activity in the appropriate chambers of the heart 12.

For arrhythmia detection, the device 10 utilizes the atrial and ventricular sensing circuits 82 and 84 to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart 12, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators 70 and 72 generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart 12 aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes and, as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

FIG. 3 illustrates the housing 40 comprising a first 122 and a second 124 enclosure halves. The first 122 and second 124 enclosure halves provide mounting surfaces for electrical components of the device 10 as well as hermetically seal a portion of the device 10 against exposure to body fluids. The first 122 and second 124 enclosure halves are made of biocompatible, electrically conductive material, such as medical grade stainless steel or titanium. In certain embodiments, the first 122 and second 124 enclosure halves are hingedly connected to each other.

The device 10 also comprises a flexible electrical interconnect 130. The flexible electrical interconnect 130 electrically interconnects the electrical components mounted in the first 122 and second 124 enclosure halves. The flexible electrical interconnect 130 is configured such that the flexible electrical interconnect 130 does not fold upon itself when the first 122 and second 124 enclosure halves are positioned adjacent each other and extends between the first 122 and second 124 enclosure halves when the first 122 and second 124 enclosure halves are distanced from each other. The flexible electrical interconnect 130 is configured such that the flexible electrical interconnect 130 is not subjected to undue mechanical strain when the first 122 and second 124 enclosure halves are adjacent each other or are distanced from each other. In one embodiment, the flexible electrical interconnect 130 describes a curved path loop substantially adjacent the periphery of an interior cavity 126 defined by the first 122 and second 124 enclosure halves when positioned adjacent each other. It is to be understood that a portion of the device 10, including the first enclosure half 122, is not shown in FIG. 4 for clarity in viewing the remaining components.

Figure 5:
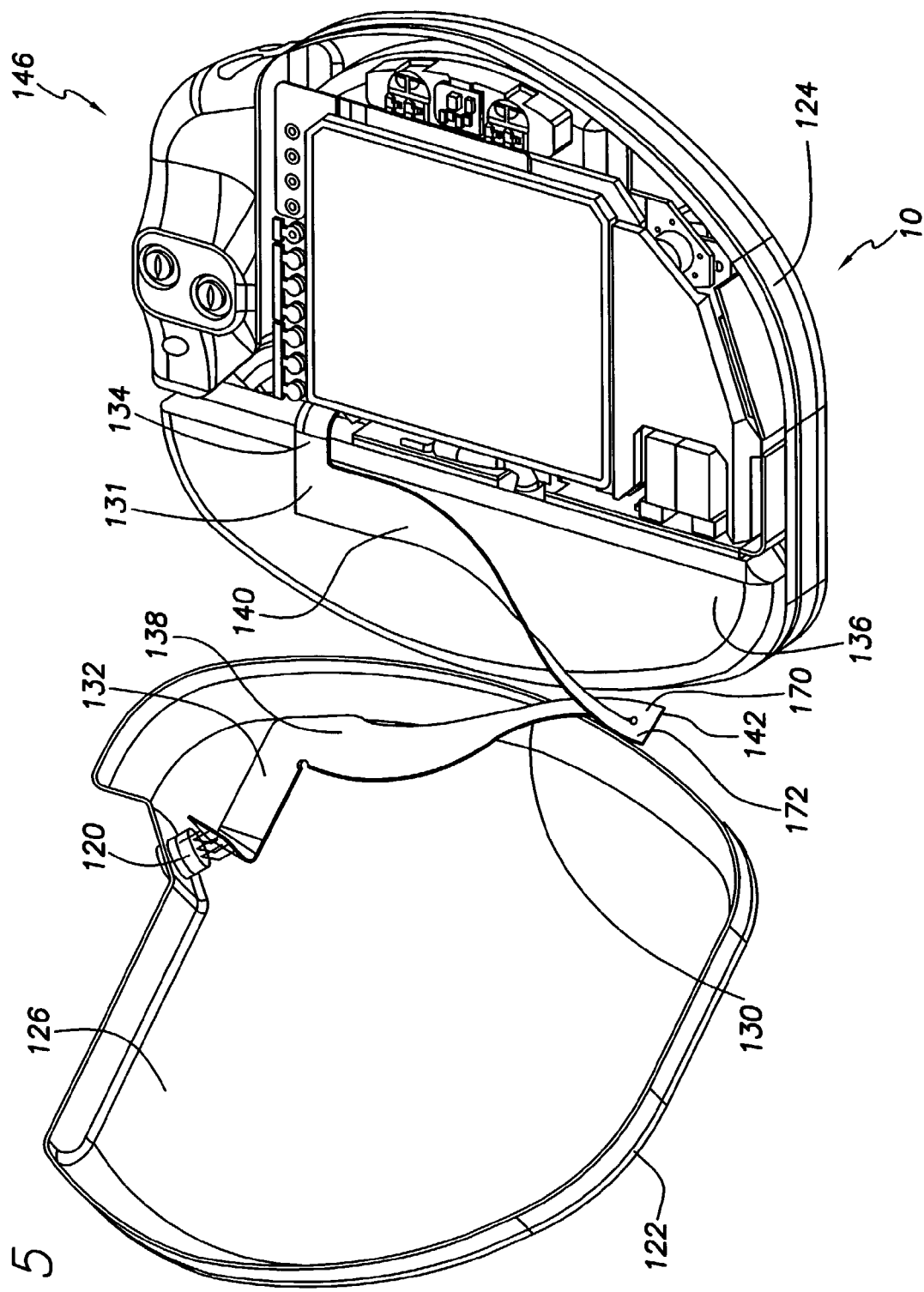
FIG. 5 is a perspective cutaway view of a cardiac device provided with one embodiment of a flexible electrical interconnect in an open position.

FIGS. 4 and 5 illustrate one embodiment of the housing 40 comprising the first 122 and second 124 enclosure halves. The first 122 and second 124 enclosure halves are generally oblate and concave in contour and are configured to closely mate together so as to hermetically seal together and thereby define the sealed interior cavity 126 in a closed configuration 144 (FIG. 4). The housing 40 provides a surface for mounting the electrical components of the stimulation device 10 previously described in an open configuration 146 (FIG. 5). The hermetic seal of the first 122 and second 124 enclosure halves in the closed configuration 144 isolates the electrical components of the device 10 from body fluids that are typically found within the thoracic cavity of the implantee.

The device 10 also comprises a capacitor 136. The capacitor 136 of this embodiment, is adhered to the second enclosure half 124 in a known manner. The capacitor 136 facilitates delivery of therapeutic shocks in the manner previously described.

The device 10 also comprises the flexible electrical interconnect 130. The flexible electrical interconnect 130, of this embodiment, is a generally planar assembly with a first end 132 and a second end 134. The flexible electrical interconnect 130 comprises a flat ribbon cable comprising a plurality of electrical conductors 131 (obscured from view), each conductor 131 electrically isolated from the other conductors 131 by a bulk insulative material surrounding each conductor 131. Each conductor 131 extends from the first end 132 to the second end 134 such that electrical signals are communicated between the first 132 and second 134 ends of the flexible electrical interconnect 130 in a known manner.

The flexible electrical interconnect 130 is configured such that, in an unstressed condition as would occur in the closed configuration 144, the first end 132 is adjacent the second end 134 as illustrated in FIG. 4. In particular, the flexible electrical interconnect 130 describes a flat spiral, generally U-shaped structure approximately 0.010 inches thick by 0.50 inches wide by 1.5 inches long. It will be appreciated that the flexible electrical interconnect 130, having a thickness of only 0.010 inches occupies minimal space inside the housing 40.

A first leg 138 and a second leg 140 of the flexible electrical interconnect 130 are joined by a junction 142. The first 138 and second 140 legs are generally elongate portions of the flexible electrical interconnect 130 and the first 138 and second 140 legs extend substantially parallel to each other when the flexible electrical interconnect 130 is in the closed configuration 144 as illustrated in FIG. 4. The junction 142 is also a portion of the flexible electrical interconnect 130 and physically and electrically joins the first 138 and second 140 legs while further facilitating resilient movement of the first 138 and second 140 legs while maintaining electrical communication therebetween.

The first end 132 is physically and electrically connected to the connector 120 and the second end 134 is physically and electrically connected to electrical components mounted in the second enclosure half 124 in a known manner, such as by soldering mechanical terminations and the like. Distancing the first 122 and second 124 enclosure halves, as illustrated in FIG. 5, places the device 10 in the open configuration 146. The open configuration 146 facilitates servicing the device 10, such as replacing the battery 110, as well as installing the component parts of the device 10 during initial manufacture.

Positioning the housing 40 in the open configuration 146 distances the first 132 and second 134 ends of the flexible electrical interconnect 130 and also induces the first 138 and second 140 legs out of a parallel, planar orientation. In particular, positioning the housing 40 in the open configuration 146 partially twists the first 138 and second 140 legs and the junction 142. However, as can be seen in FIG. 5, the configuration of the flexible electrical interconnect 130 is such that placement of the first 122 and second 124 enclosure halves, as illustrated in FIG. 5, in approximately a 180° orientation induces only approximately a 90° twist in each of the first 138 and second 140 legs. Displacing the first 122 and second 124 enclosure halves in a 180° orientation is the most that would typically be required for normal manufacture and servicing of the device 10. The 90° twist in each of the first 138 and second 140 legs does not unduly stress the flexible electrical interconnect 130 and the flexible electrical interconnect 130, of this configuration, can withstand repeated cycling between the closed 144 and open 146 configurations as herein described.

More specifically, as is illustrated in FIG. 4, each of the conductors 131 within the flexible electrical interconnect 130 extend in a first direction 161 in the first leg 138 of the flexible electrical interconnect when the enclosure 40 is in the closed configuration. Similarly, each of the conductors in the second leg 140 extend in a second direction 163 that is preferably parallel to the first direction 161. However, each of the conductors 131 in the junction section 142 travel in a third direction 165 that is transverse to the first 161 and second 163 directions. The length of the portion of the conductors 131 extending in the transverse direction 165 in the junction section 142 of the flexible electrical interconnect 130 are preferably individually sized so that the first and second legs 138, 140 of electrical interconnect 130 are positioned immediately adjacent each other in the manner shown in FIG. 4 when the enclosure 40 is in the closed configuration 144 to thereby reduce the amount of space within the enclosure 40 that is occupied by the electrical interconnect 130.

It will be appreciated that the directions 161 and 163 need only be parallel in a single plane to permit the flexible electrical interconnect 130 to have reduced thickness when the enclosure 40 is in the closed configuration 144. Each of the legs 138, 140 may be slightly mis-aligned in a direction perpendicular to the plane of the enclosure 40 as the connection point at the ends of the legs 138, 140 are offset from each other in the vertical direction. By positioning the legs 138, 140 so as to be side by side, with the transverse section 142 laterally spanning the two legs, the electrical interconnect 130 does not require the legs 138, 140 to be stacked on top of each other and thereby results in less volume between the two enclosure halves 122, 124 to be occupied by the electrical interconnect 130.

As is also illustrated in FIG. 4, each of the conductors 131 in the electrical interconnect 130 achieves a 180 degree change of direction in two separate smaller angle turns. Specifically, the conductors 131 in the leg 138 are extending in a direction that, in at least one plane, is 180 degrees different than the direction of the conductors 131 in the leg 140. By forming the electrical interconnect 130 to have the transverse junction section 142, that extends in the transverse direction 165, each of the conductors 131 achieves the 180 degree change of direction through a first interconnection 170 between the first leg 138 and the junction section 142 and a second interconnection 172 between the junction section 142 and the second leg 140. In the embodiment illustrated in FIG. 4, the first and second interconnections 170, 172 result in a 90 degree turn of the conductors respectively. By dividing the change of direction between two separate interconnections 170, 172, mechanical strain on the conductors 131 is reduced. Specifically, since the conductors 131 have two reduced bend points as opposed to a single higher angle bend point, the likelihood that the conductors 131 will break or separate at the bend point is reduced.

Moreover, as is illustrated in FIG. 5, when the enclosure halves 122, 124 are separated, the lateral separation between the legs 138, 140 that permits the separation is achieved by both rotating the legs 138, 140 about their interconnection with the junction section 142 and also by bending the legs 138, 140 in a direction that is perpendicular to the plane of the legs 138, 140 in the manner illustrated in FIG. 5. Hence, two separate degrees of motion provide the increase in the lateral separation between the legs 138, 140 which further reduces the tension on the conductors 131 contained within the interconnect 130.

Thus, the flexible electrical interconnect 130 of this embodiment interconnects electrical components mounted in both the first 122 and second 124 enclosure halves. The flexible electrical interconnect 130 is a thin, planar assembly and thus occupies minimal space inside the housing 40. The flexible electrical interconnect 130 is easily installed with common tools and procedures already known in the art. The flexible electrical interconnect 130 is also not under undue stress in either the closed 144 or open 146 configurations and thus avoids the high stress bending of flex cables in the prior art.

It should be appreciated that, although the embodiment described herein is with respect to a cardiac stimulation device 10, the flexible electrical interconnect 120 can be readily adapted to other implanted medical devices by one of ordinary skill in the art. In alternative embodiments, the first 122 and second 124 enclosure halves are made of electrically non-conductive material.

Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. An implantable medical device comprising:
a first enclosure half;
a second enclosure half adapted to mate with the first enclosure half so as to define a housing with an interior cavity;
a plurality of electrical components mounted in the first enclosure half;
a plurality of electrical components mounted in the second enclosure half shell;
a flexible electrical interconnect electrically interconnecting electrical components mounted in the first enclosure half with electrical components mounted in the second enclosure half, wherein the flexible electrical interconnect assumes a first configuration such that portions of the flexible electrical interconnect are laterally spaced from each other so as to not overlap when the first and second enclosure halves are mated, and a second configuration when the first and second enclosure halves are distanced.

2. The device of claim 1, wherein the first and second enclosure halves are hingeably connected so as to be movable between the first configuration and the second configuration.

3. The device of claim 1, wherein the first and second enclosure halves define a hermetically sealed environment in the first configuration.

4. The device of claim 3, wherein the first and second enclosure halves are formed of an electrically conductive material.

5. The device of claim 1, wherein the plurality of electrical components mounted in the first and second enclosure halves are arranged to provide the electrical functionality of an implantable cardiac stimulation device.

6. The device of claim 1, wherein the flexible electrical interconnect includes a plurality of conductors positioned adjacent each other in a planar configuration wherein the plurality of conductors are insulated from each other.

7. The device of claim 6, wherein the flexible electrical interconnect comprises:
a first leg;
a second leg;
an interconnecting section interconnecting the first and the second leg, wherein the first leg and the second leg in the first configuration are positioned so as to extend in parallel directions in at least one plane with the interconnecting section extending in a transverse direction to the parallel directions of the conductors in the first and second legs.

8. The device of claim 7, wherein the first leg and the second leg are positioned immediately adjacent each other so as to be positioned side by side when the first and second enclosure halves are in the first configuration.

9. The device of claim 7, wherein the conductors in the flexible electrical interconnect are routed through the flexible electrical interconnect through a path that results in the conductors changing in direction in at least one plane and wherein the change in direction in at least one plane is divided into a plurality of changes of direction to thereby reduce the bending forces exerted on the conductors and insulation of the flexible electrical interconnect.

10. The device of claim 9, wherein the conductors have a first change of direction at the junction of the first leg and the interconnecting section and a second change of direction at the junction of the second leg and the interconnecting section.

11. The device of claim 10, wherein the first and second changes of direction are approximately 90 degrees each resulting in an aggregate change of direction of approximately 180 degrees.

12. The device of claim 7, wherein the first and second leg are rotated with respect to the interconnecting section and moved laterally outward with respect to the interconnecting section in the second configuration.

13. An implantable cardiac stimulation device comprising:
a first enclosure half having an interior surface;
a second enclosure half having an interior surface that mates with the first enclosure half so as to define a housing with an interior cavity wherein the first and second enclosure halves are connectable so as to permit the first and second enclosure halves to be in a closed configuration thereby hermetically sealing the cavity and an open configuration wherein the interior surfaces of the first and second enclosure halves are laterally spaced from each other to permit access thereto;
a plurality of electrical components mounted in the first and second enclosure halves, wherein the plurality of electrical components provide the electrical functionality of the implantable cardiac stimulation device;
a generally planar, flexible electrical interconnect electrically interconnecting electrical components mounted in the first enclosure half with electrical components mounted in the second enclosure half wherein the flexible electrical interconnect has a plurality of electrical conductors positioned therein and wherein the flexible electrical interconnect includes a first and second legs having outer ends respectively attached to the first and second enclosure halves wherein the first and second legs have inner ends that are coupled together and in the first configuration the first and second legs are offset from each other so as to not overlap and wherein the first and second legs are movable with respect to their interconnection such the outer ends of the first and second legs can be spaced from each other to permit the first and second enclosure halves to be positioned in the second configuration.

14. The device of claim 13, wherein the first and second enclosure halves are formed of an electrically conductive material.

15. The device of claim 13, wherein the planar flexible electrical interconnect includes an interconnecting section that interconnects the inner ends of the first and second legs.

16. The device of claim 15, wherein the first leg and the second leg in the first configuration are positioned so as to extend in parallel directions in at least one plane with the interconnecting section extending in a transverse direction to the parallel directions of the conductors in the first and second legs.

17. The device of claim 16, wherein the first leg and the second leg are positioned immediately adjacent each other so as to be positioned side by side when the first and second enclosure halves are in the first configuration.

18. The device of claim 16, wherein the conductors in the planar flexible electrical interconnect are routed through the planar flexible electrical interconnect through a path that results in the conductors changing in direction in at least one plane and wherein the change in direction in at least one plane is divided into a plurality of changes of direction to thereby reduce the bending forces exerted on the conductors and insulation of the planar flexible electrical interconnect.

19. The device of claim 18, wherein the conductors have a first change of direction at the junction of the first leg and the interconnecting section and a second change of direction at the junction of the second leg and the interconnecting section.

20. The device of claim 19, wherein the first and second changes of direction are approximately 90 degrees each resulting in an aggregate change of direction of 180 degrees.

21. The device of claim 20, wherein the first and second leg are rotated with respect to the interconnecting section and moved laterally outward with respect to the interconnecting section in the second configuration.

22. A container assembly for an implantable medical device the assembly comprising:
a first enclosure half defining a partially enclosed space that is adapted to contain electronic components for the implantable medical device;
a second enclosure half defining a partially enclosed space that is adapted to contain electronic components for the implantable medical device, wherein the first and second enclosure halves can be coupled together to define a housing with an enclosed space such that the electronic circuitry is enclosed within the enclosed space;
a flexible electrical interconnect assembly having a plurality of conductors wherein the flexible electrical interconnect assembly interconnects the first and second enclosure halves so as to permit electrical interconnection between the electronic components positioned within the partially enclosed spaces of the first and second enclosure halves, wherein the flexible electrical interconnect assembly comprises first and second leg members each having a first and a second end and an interconnection section interconnecting the first ends of the first and second leg members wherein the interconnecting section extends in a direction that is perpendicular to the direction of the first and second leg members such that when the first enclosure half and the second enclosure half are coupled together, the first and second leg halves are offset from each other in a direction parallel to the direction of the interconnecting section.

23. The device of claim 22, wherein the first and second enclosure halves define a hermetically sealed environment when coupled together.

24. The device of claim 23, wherein the first and second enclosure halves are formed of an electrically conductive material.

25. The device of claim 22, wherein the first leg and the second leg are positioned immediately adjacent each other so as to be positioned side by side when the first and second enclosure halves are coupled together.

26. The device of claim 25, wherein the conductors in the flexible electrical interconnect assembly are routed through the flexible electrical interconnect assembly along a path that results in the conductors changing in direction in at least one plane and wherein the change in direction in at least one plane is divided into a plurality of changes of direction to thereby reduce the bending forces exerted on the conductors and insulation of the planar flexible electrical interconnect.

27. The device of claim 26, wherein the conductors have a first change of direction at the junction of the first leg and the interconnecting section and a second change of direction at the junction of the second leg and the interconnecting section.

28. The device of claim 27, wherein the first and second changes of direction are approximately 90 degrees each resulting in an aggregate change of direction of 180 degrees.

29. The device of claim 22, wherein the first and second leg are rotated with respect to the interconnecting section and moved laterally outward with respect to the interconnecting section when the first and second enclosure halves are separated from each other and are laterally spaced from each other.

* * * * *